(12) United States Patent
Cross, Jr. et al.

(10) Patent No.: US 9,688,590 B2
(45) Date of Patent: Jun. 27, 2017

(54) PRODUCTION OF JET AND OTHER HEAVY FUELS FROM ISOBUTANOL

(75) Inventors: William M. Cross, Jr., Kemah, TX (US); Gary G. Podrebarac, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 1220 days.

(21) Appl. No.: 13/104,572

(22) Filed: May 10, 2011

(65) Prior Publication Data

US 2011/0282117 A1 Nov. 17, 2011

Related U.S. Application Data

(60) Provisional application No. 61/333,111, filed on May 10, 2010.

(51) Int. Cl.
*C07C 1/24* (2006.01)
*C07C 2/04* (2006.01)
(Continued)

(52) U.S. Cl.
CPC .............. *C07C 5/03* (2013.01); *C07C 1/24* (2013.01); *C07C 2/12* (2013.01); *C07C 2/28* (2013.01); *C10G 3/42* (2013.01); *C10G 69/126* (2013.01); *C07C 2521/04* (2013.01); *C07C 2521/06* (2013.01); *C07C 2521/08* (2013.01); *C07C 2521/12* (2013.01); *C07C 2521/16* (2013.01); *C07C 2523/28* (2013.01); *C07C 2523/30* (2013.01); *C07C 2523/42* (2013.01); *C07C 2523/44* (2013.01); *C07C 2523/75* (2013.01);
(Continued)

(58) Field of Classification Search
CPC .... C07C 2/00; C07C 2/02; C07C 2/04; C07C 2/06; C07C 11/09; C07C 29/60
USPC ....... 585/312, 313, 325, 327, 329, 330, 609, 585/639, 733, 254, 255, 508, 510, 310, 585/315
See application file for complete search history.

(56) References Cited

U.S. PATENT DOCUMENTS 2,366,007 A    12/1944  D'Alelio
2,945,906 A *   7/1960  Kroeper .................. B01J 21/20
                                                   502/251
(Continued)

FOREIGN PATENT DOCUMENTS

DE           908247 C      4/1954
WO       2011/143215 A2   11/2011

OTHER PUBLICATIONS

Talwalkar et al., "Kinetic Studies on the Dimerization of Isobutene with Ion-Exchange Resin in the Presence of Water as a Selectivity Enhancer", Ind. Eng. Chem. Res. 2006, 45, 1312-1323.*
(Continued)

*Primary Examiner* — In Suk Bullock
*Assistant Examiner* — Philip Louie
(74) *Attorney, Agent, or Firm* — Osha Liang LLP

(57) ABSTRACT

A process for the production of jet and other heavy fuels, the process including: contacting at least one C3 to C5 isoalkanol with a first catalyst to convert at least a portion of the isoalkanol to isoalkene, isoalkene dimers, and water; contacting at least a portion of the isoalkene dimers with a second catalyst to convert at least a portion of the isoalkene dimers to isoalkene trimers; hydrotreating the isoalkene trimers to form isoalkanes useful as a jet fuel, kerosene, or other heavy fuels.

23 Claims, 5 Drawing Sheets

(51) Int. Cl.
*C07C 2/08* (2006.01)
*C07C 5/03* (2006.01)
*C07C 2/12* (2006.01)
*C07C 2/28* (2006.01)
*C10G 3/00* (2006.01)
*C10G 69/12* (2006.01)

(52) U.S. Cl.
CPC .. *C07C 2523/755* (2013.01); *C07C 2523/882* (2013.01); *C07C 2523/883* (2013.01); *C07C 2523/888* (2013.01); *C07C 2529/08* (2013.01); *C07C 2529/18* (2013.01); *C07C 2529/50* (2013.01); *C07C 2529/60* (2013.01); *C07C 2529/70* (2013.01); *C07C 2531/10* (2013.01); *C10G 2300/1088* (2013.01); *C10G 2300/4081* (2013.01); *C10G 2300/4087* (2013.01); *C10G 2400/08* (2013.01); *Y02P 20/127* (2015.11)

(56) References Cited

U.S. PATENT DOCUMENTS

| | | | |
|---|---|---|---|
| 4,100,220 A | 7/1978 | Bowman et al. | |
| 4,230,533 A | 10/1980 | Giroux | |
| 4,242,530 A | 12/1980 | Smith, Jr. | |
| 4,331,824 A | 5/1982 | Ikeda et al. | |
| 4,375,576 A | 3/1983 | Smith, Jr. | |
| 4,443,559 A | 4/1984 | Smith, Jr. | |
| 4,551,567 A | 11/1985 | Smith, Jr. | |
| 4,582,569 A | 4/1986 | Jenkins | |
| 4,629,710 A | 12/1986 | Smith, Jr. | |
| 4,826,574 A | 5/1989 | Gourlia et al. | |
| 5,003,124 A | 3/1991 | Smith, Jr. et al. | |
| 5,057,468 A | 10/1991 | Adams | |
| 5,262,012 A | 11/1993 | Smith, Jr. | |
| 5,266,546 A | 11/1993 | Hearn | |
| 5,339,648 A | 8/1994 | Lockett et al. | |
| 5,348,710 A | 9/1994 | Johnson et al. | |
| 5,730,843 A | 3/1998 | Groten et al. | |
| 5,755,933 A | 5/1998 | Ognisty et al. | |
| 5,877,372 A * | 3/1999 | Evans et al. | 585/510 |
| 6,335,473 B1 | 1/2002 | Bakshi et al. | |
| 6,376,731 B1 | 4/2002 | Evans et al. | |
| 6,689,927 B1 | 2/2004 | Frame et al. | |
| 6,740,783 B1 | 5/2004 | Jun et al. | |
| 6,774,275 B2 | 8/2004 | Smith, Jr. et al. | |
| 6,858,770 B2 | 2/2005 | Smith, Jr. et al. | |
| 6,936,742 B2 | 8/2005 | Smith, Jr. | |
| 6,995,296 B2 | 2/2006 | Smith, Jr. et al. | |
| 7,026,517 B2 | 4/2006 | Groten et al. | |
| 7,145,049 B2 | 12/2006 | Loescher et al. | |
| 7,250,542 B2 | 7/2007 | Smith, Jr. et al. | |
| 7,268,268 B2 * | 9/2007 | al-Soufi et al. | 585/510 |
| 7,288,693 B2 | 10/2007 | Smith, Jr. et al. | |
| 7,319,180 B2 | 1/2008 | Smith, Jr. et al. | |
| 2004/0006252 A1 | 1/2004 | Smith | |
| 2004/0210093 A1 | 10/2004 | Groten et al. | |
| 2005/0049448 A1* | 3/2005 | Loescher et al. | 585/533 |
| 2005/0222475 A1* | 10/2005 | Duplan et al. | C07C 11/06 585/329 |
| 2006/0030741 A1 | 2/2006 | Smith et al. | |
| 2007/0092957 A1 | 4/2007 | Donaldson et al. | |
| 2007/0161843 A1 | 7/2007 | Smith et al. | |
| 2008/0013274 A1 | 1/2008 | Jobs et al. | |
| 2008/0015395 A1 | 1/2008 | D'amore et al. | |
| 2008/0045754 A1 | 2/2008 | D'Amore et al. | |
| 2008/0045763 A1 | 2/2008 | Cross et al. | |
| 2008/0064911 A1 | 3/2008 | Loescher et al. | |
| 2008/0234523 A1 | 9/2008 | Manzer et al. | |
| 2009/0030239 A1 | 1/2009 | D'Amore et al. | |
| 2009/0099401 A1 | 4/2009 | D'Amore et al. | |
| 2009/0178955 A1 | 7/2009 | Ryu | |
| 2009/0299109 A1 | 12/2009 | Gruber et al. | |
| 2010/0137668 A1* | 6/2010 | Loescher et al. | 585/504 |
| 2011/0087000 A1* | 4/2011 | Peters et al. | 528/308.3 |
| 2011/0288352 A1* | 11/2011 | Peters et al. | 585/14 |

OTHER PUBLICATIONS

International Search Report and Written Opinion issued Jan. 18, 2012 in corresponding International Application No. PCT/US2011/035919 (12 pages).

Office Action issued Aug. 30, 2013 in corresponding Canadian application No. 2,797,424 (3 pages).

Office Action issued Jun. 12, 2014 in corresponding Canadian application No. 2,797,424 (2 pages).

Substantive Examination Report issued Jan. 15, 2014 in corresponding Malaysian application No. PI 2012004872 (3 pages).

Correspondence reporting a Second Office Action issued Sep. 17, 2014 in corresponding Chinese application No. 201180023127.X (8 pages).

* cited by examiner

PRODUCTION OF JET AND OTHER HEAVY FUELS FROM ISOBUTANOL

FIELD OF THE DISCLOSURE

Embodiments disclosed herein relate generally to a process for the production of fuels. More specifically, embodiments disclosed herein relate to processes for the conversion of isoalkanols to form jet and other heavy fuels.

BACKGROUND

Isobutanol can be formed from the fermentation of sugars which can be formed via the breakdown of cellulose. For example, solutions of up to approximately 2% by weight isobutanol in microbial growth have been produced in certain fermentation processes (Fraces Arnold, "The Race for New Biofuels," Engineering & Science, No. 2, 2008). U.S. Patent Application Publication No. 20070092957 describes fermentatively producing isobutanol using recombinant microorganisms.

As microbes are further developed to withstand higher concentrations of isobutanol, it can be envisioned that isobutanol may compete with ethanol as a potential-fuel component or chemical feedstock derived from renewable resources. Unfortunately, there exist concerns regarding direct blending of isobutanol and other higher alcohols into the gasoline pool due to odor and automotive component compatibility issues. For this reason, there is interest in conversion of light alcohols into feedstocks for conversion into fuels, petrochemicals, or other valuable end products.

U.S. Patent Application Publication Nos. 20090099401, 20090030239, 2008013274, 20080045754, 20080015395, 20080234523, and others, each filed by E.I. Dupont de Nemours and Company, Wilmington, Del., are directed to the conversion of bio-derived isobutanol to butenes and isooctenes, among other end products. Each of these processes react isobutanol over a homogeneous or heterogeneous acid catalyst to form the desired reaction product, either a butene or an isooctene (diisobutylene).

Unlike tertiary butanol, which can be readily converted via dehydration into its constituent isobutylene and then into fuel blend components, such as diisobutylene, as disclosed in U.S. Pat. No. 6,936,742, the conversion of other light alcohols often requires higher activity catalysts and more severe process conditions. Significant recycle rates may also be required to result in acceptable conversion levels. Additionally, with bio-derived alcohols, water may be present with the feed, and separation is often difficult due to the components having closer relative volatilities and potential for forming various azeotropes.

Accordingly, there exists a need for processes for the conversion of light alcohols such as isobutanol into useful feedstocks for conversion into fuels, petrochemicals, or other valuable end products.

SUMMARY OF THE CLAIMED EMBODIMENTS

In one aspect, embodiments disclosed herein relate to a process for the production of jet and other heavy fuels, the process including: contacting at least one C3 to C5 isoalkanol with a first catalyst to convert at least a portion of the isoalkanol to isoalkene, isoalkene dimers, and water; contacting at least a portion of the isoalkene dimers with a second catalyst to convert at least a portion of the isoalkene dimers to isoalkene trimers; hydrotreating the isoalkene trimers to form isoalkanes useful as a jet fuel, kerosene, or other heavy fuels.

In another aspect, embodiments disclosed herein relate to a process for the production of jet and other heavy fuels, the process including: feeding isobutanol to a catalytic distillation reactor system having at least one reaction zone containing a first catalyst; concurrently in the catalytic distillation reactor system: contacting the isobutanol with the first catalyst to convert at least a portion of the isobutanol to isobutylene, dimers of isobutylene, and water; fractionating the isobutylene and the water from the dimers of isobutylene; recovering the isobutylene and the water as an overheads fraction from the catalytic distillation reactor system; recovering the isobutylene dimers as a bottoms fraction from the catalytic distillation reactor system; feeding the bottoms fraction to a first reactor having at least one reaction zone containing a second catalyst; contacting the bottoms fraction with the second catalyst to convert at least a portion of the isobutylene dimers to trimers of isobutylene; recovering an effluent from the reactor comprising the isobutylene trimers and any unreacted isobutylene dimers; feeding hydrogen and at least a portion of the effluent from the first reactor to a second reactor having at least one reaction zone containing a third catalyst; contacting the hydrogen and the effluent from the first reactor with the third catalyst to hydrogenate at least a portion of the isobutylene trimers to C12 paraffins and to hydrogenate at least a portion of any unreacted isobutylene dimers in the effluent to C8 paraffins; recovering an effluent from the second reactor comprising the C8 and C12 paraffins; separating the effluent from the second reactor in a fractionators; recovering the C8 paraffins as an overheads fraction from the fractionator; and recovering the C12 paraffins as a bottoms fraction from the fractionator.

In another aspect, embodiments disclosed herein relate to a process for the production of jet and other heavy fuels, the process including: feeding isobutanol to a catalytic distillation reactor system having at least one reaction zone containing a first catalyst; concurrently in the catalytic distillation reactor system: contacting the isobutanol with the first catalyst to: a) convert at least a portion of the isobutanol to isobutylene and water, b) react the isobutylene produced to form oligomers of isobutylene, and c) reacting a portion of the isobutylene or oligomers of isobutylene produced with isobutanol to form ethers; fractionating the isobutylene and the water from the ethers and the oligomers of isobutylene; recovering the ethers and the isobutylene oligomers as a bottoms fraction from the catalytic distillation reactor system; recovering the isobutylene and the water as an overheads fraction from the catalytic distillation reactor system; separating the overheads fraction to recover a water fraction and an isobutylene fraction; feeding the isobutylene fraction to a first reactor having at least one reaction zone containing a second catalyst; contacting the isobutylene fraction with the second catalyst to convert at least a portion of the isobutylene to oligomers of isobutylene; recovering an effluent from the first reactor comprising the isobutylene oligomers and any unreacted isobutylene; feeding hydrogen and at least a portion of the effluent from the first reactor to a second reactor having at least one reaction zone containing a third catalyst; contacting the hydrogen and the effluent from the first reactor with the third catalyst to hydrogenate at least a portion of the isobutylene oligomers to paraffins; recovering an effluent from the second reactor comprising C8 and C12 paraffins; separating the effluent from the second reactor in a fractionator; recovering the C8 paraffins as an overheads fraction from the fractionator; and recovering the C12 paraffins as a bottoms fraction from the fractionator.

Other aspects and advantages will be apparent from the following description and the appended claims.

DETAILED DESCRIPTION

Figure 1:
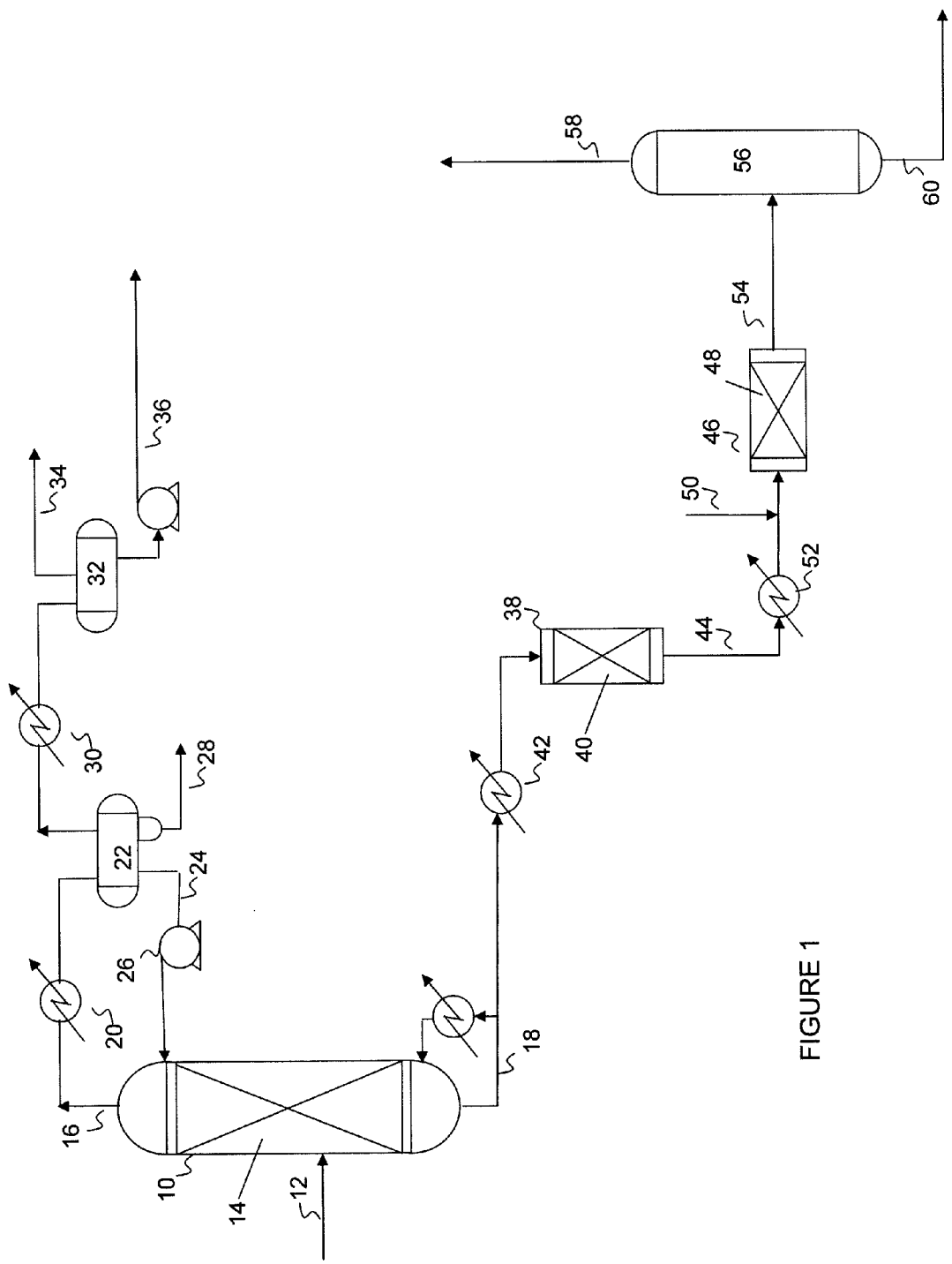
FIG. 1 is a simplified process flow diagram of a process for the production of jet and other heavy fuels according to embodiments disclosed herein.

Within the scope of this application, the expression "catalytic distillation reactor system" denotes an apparatus in which the catalytic reaction and the separation of the products take place at least partially simultaneously. The apparatus may comprise a conventional catalytic distillation column reactor, where the reaction and distillation are concurrently taking place at boiling point conditions, or a distillation column operatively connected with at least one side reactor to which a sidedraw from the distillation column is introduced as a feed and from which a reactor effluent is withdrawn and returned to the distillation column, where the side reactor may be operated as a liquid phase reactor, a vapor phase reactor, or a boiling point reactor. While both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein.

Processes disclosed herein may include any number of reactors, including catalytic distillation reactor systems, both up-flow and down-flow. Use of catalytic distillation reactor systems may prevent foulants and heavy catalyst poisons in the feed from building up within the reaction zone(s). In addition, clean reflux may continuously wash the catalytic distillation structure in the reaction zone. These factors combine to provide a long catalyst life. The heat of reaction evaporates liquid and the resulting vapor is condensed in the overhead condenser to provide additional reflux. The resulting temperature profile in the reaction zone in the catalytic distillation reaction system is much closer to an isothermal catalyst bed rather than the adiabatic temperature increase typical of conventional fixed bed reactors.

Other reactors useful in embodiments disclosed herein may include traditional fixed bed reactors, boiling point reactors, and pulsed flow reactors, where the reactant flow and product flow may be co-current or counter-current. Boiling point and pulsed flow reactors may also provide for a continuous washing of the catalyst in addition to capturing at least a portion of the heat of reaction through evaporation, allowing for an improved reactor temperature profile as compared to conventional fixed bed reactors. Reactors useful in embodiments disclosed herein may be used as a stand-alone reactor or may be used in combination with one or more reactors of the same or different type.

Any type of reactor may be used to carry out the reactions described herein. The examples of reactors suitable for carrying out the reactions of embodiments herein may include distillation column reactors, divided wall distillation column reactors, traditional tubular fixed bed reactors, bubble column reactors, slurry reactors equipped with or without a distillation column, pulsed flow reactors, catalytic distillation columns wherein slurry solid catalysts flow down the column, conventional fixed bed reactors, or any combination of these reactors. Multiple-reactor systems useful in embodiments disclosed herein may include a series of the same type of reactor or reactors in parallel, or different types of reactors in series, for the respective reaction zones. A person of ordinary skill in the art would recognize that other types of reactors may also be used.

In one aspect, embodiments herein relate to processes for the production of jet and other heavy fuels from alcohols. More specifically, embodiments disclosed herein relate to processes for the conversion of isoalcohols, such as isobutanol, to form isoolefins and dimers of isoolefins, with the subsequent conversion of the dimers to form trimers of the isoolefins.

Isoalkenes and dimers of isoalkenes may be prepared by the dehydration of an isoalcohol to form an isoalkene, followed by the dimerization of the isoalkenes to form isoalkene dimers. Both the dehydration and dimerization reaction may be catalyzed using an acid catalyst, such as sulfuric acid, or other catalysts as described below. Side reactions may include the formation of dialkyl ethers, oligomers, aromatics, and coke, which typically cause fouling of the catalyst.

Alcohols that may be used in embodiments disclosed herein include C3 to C6 alcohols, among others. For example, propanol, isopropanol, n-butanol, 2-butanol, isobutanol, pentanols, isopentanol, hexanols, and isohexanols, among others, may be used. In some embodiments, isobutanol is the preferred alcohol. Alcohols may also be used in admixture, such as an admixture of C4 and C5 isoalcohols, or an admixture of C3, C4, and/or C5 alcohols. Use of the respective alcohols may depend on the selectivity of the catalyst to produce the desired isoalkenes and isoalkene dimers, the concentration of the higher alcohol, the resulting boiling point of the dialkyl ether, and the potential for the reactants and/or products to form an azeotrope with water, among other factors. For ease of separations, and to obtain substantially pure product streams, the boiling point of resulting dimers should be greater than the boiling point of water and the feed alcohol(s) under column operating conditions.

In some embodiments, the alcohols useful in embodiments disclosed herein may include bio-alcohols, such as bio-derived isobutanol, for example. Bio-alcohols are a feed material that may be derived from renewable resources, such as corn, corn stalks, corn cobs, lignocellulose, sugarcane, sugar beets, and wheat, among others. While direct blending of the alcohol into gasoline may be performed by simple mixing, the odor, vapor pressure, or material compatibility of the gasoline may be negatively affected due to the alcohol. Use of bio-alcohols according to embodiments disclosed herein may provide an alternative method to incorporate a renewable resource, bio-alcohol, as a gasoline feed stock, without the undesirable effects.

In some embodiments, the alcohol or mixture of alcohols may be derived from a renewable resource via a fermentation process, such as described in U.S. Patent Application Publication No. 20070092957, which is incorporated herein by reference to the extent not contradictory to embodiments disclosed herein. Further, the resulting fermentation product may be worked up to achieve a wet or dry alcohol, such as described in U.S. Patent Application Publication No. 20090030239 and others as mentioned above, each of which is incorporated herein by reference to the extent not contradictory to embodiments disclosed herein.

Fermentation methodology is well known in the art, and can be carried out in a batch-wise, continuous or semi-continuous manner. As is well known to those skilled in the art, the concentration of isobutanol in the fermentation broth produced by any process will depend on the microbial strain and the conditions, such as temperature, growth medium, mixing and substrate, under which the microorganism is grown.

Following fermentation, the fermentation broth from the fermentor can be used in embodiments disclosed herein. In some embodiments, the fermentation broth is subjected to a refining process to produce an aqueous stream comprising an enriched concentration of isobutanol. As used herein, "refining process" refers to a process comprising one unit operation or a series of unit operations that allows for the purification of an impure aqueous stream comprising isobutanol yielding an aqueous stream comprising substantially pure isobutanol. For example, in one embodiment, the refining process yields a stream that comprises at least about 5% water and isobutanol, but is substantially free of ethanol that may have been present in the fermentation broth.

Refining processes used in the production of alcohols typically utilize one or more distillation steps as a means for recovering a fermentation product. It is expected, however, that fermentative processes will produce isobutanol at very low concentrations relative to the concentration of water in the fermentation broth. This can lead to large capital and energy expenditures to recover the isobutanol by distillation alone. As such, other techniques can be used either alone or in combination with distillation as a means of concentrating the dilute isobutanol product. In such processes where separation techniques are integrated with the fermentation step, cells are often removed from the stream to be refined by centrifugation or membrane separation techniques, yielding a clarified fermentation broth. These cells are then returned to the fermentor to improve the productivity of the isobutanol fermentation process. The clarified fermentation broth is then subjected to such techniques as pervaporation, gas stripping, liquid-liquid extraction, perstraction, adsorption, distillation, or combinations thereof. Depending on product mix, these techniques can provide a stream comprising water and isobutanol suitable for use in the processes disclosed herein. If further purification is necessary, the stream can be treated further by distillation to yield an aqueous or dry isobutanol stream.

Alcohol feeds useful in embodiments disclosed herein may contain impurities, such as water. For example, alcohols may contain a certain amount of water. Typically, the water is removed from the alcohol. However, as water is a byproduct of the alcohol dehydration reaction, alcohol feeds used in embodiments disclosed herein may include water as an impurity. Excessive water in the feed may decrease pre-reactor conversion equilibrium, discussed below, and may result in increased reboiler duties, but water as a feed impurity may be tolerated in systems described herein.

In some embodiments, alcohol feeds may include up to 40 weight percent water; up to 30 weight percent water in other embodiments; up to 20 weight percent water in other embodiments; up to 10 weight percent water in other embodiments; up to 5 weight percent water in other embodiments; and up to 2 weight percent water in yet other embodiments. In other embodiments, alcohol feeds may be substantially pure alcohol or alcohol mixtures. In other embodiments, alcohol feedstocks useful in embodiments disclosed herein may contain from 0.1 to 100 wt. % alcohol and from 0 to 99.9 wt. % water. In other embodiments, the alcohol feedstock may contain from 10 to 100 wt. % alcohol; from 25 to 100 wt. % alcohol in other embodiments; and from 50 to 95 wt. % alcohol in yet other embodiments. The amount of water that may be used within the catalytic reaction zones may depend on (1) the reaction equilibrium constant and (2) the strength/activity of the acid catalyst for conversion. For example, as one moves from resin type catalysts to stronger sulfuric or hydrochloric acid concentrations, activity can be maintained at higher water concentrations. Acid resin catalysts will be more susceptible to loss in catalyst activity as one moves to larger quantities of water at elevated temperatures.

As described above, alkyl alcohols may be fed to a distillation column reactor system, where the alcohols contact a catalyst and reacts to form alkenes and/or isoalkenes, dimers of the alkenes and/or isoalkenes, and water. The dimers, boiling at a temperature higher than water, may be recovered as a bottoms fraction. Water and the alkenes or isoalkenes may be recovered as an overhead fraction.

In some embodiments, the distillation column reactor system may include a distillation column reactor. A distillation column reactor may include one or more distillation reaction zones, where a catalyst structure may also serve as a distillation structure, resulting in the concurrent reaction and fractionation of the reactants and products. Feed and distillation reaction zone location may depend upon the respective boiling points of the reactants and products.

Distillation reaction zones may also be located in a portion of a divided wall distillation column. Divided wall distillation columns are described in, for example, U.S. Pat. Nos. 4,230,533; 4,582,569; 4,826,574; 5,339,648, 5,755,933, and 7,026,517. Divided wall columns may include distillation vessels having a vertical partition separating one side from the other for a portion or all of the height of the vessel. The divided wall column may have a common rectification section, a common stripping section, or both. In some embodiments disclosed herein, the distillation column reactor may be a divided wall column, where the divided wall column comprises at least one catalytic reaction zone. In other embodiments, the feed may be to a non-catalytic distillation zone of the divided wall column.

In other embodiments, the distillation column reactor system may include a primary distillation column and a side reactor. Feed for the side reactor may include a side draw from the primary distillation column, and a product stream may be returned to the primary distillation column. Side draw and return locations may depend on the respective boiling points of the reactants and products. In some embodiments, the side reactor may include a fixed bed reactor; in other embodiments, the side reactor may include a distillation column reactor, having both vapor and liquid feed and return to the primary distillation column.

In various embodiments, heat transfer systems may be used to integrate the heating and cooling of the feed and product streams. For example, the alcohol feed may be heated using at least a portion of the overhead stream, at least a portion of the bottoms stream, or a combination thereof. Other heat integration configurations may also be used.

In other embodiments, a pre-reactor may be used to convert at least a portion of the alcohol feed to alkene/isoalkene or dimers of the alkene/isoalkene. For example, a fixed bed reactor may be used to convert a portion of the alcohol to alkene/isoalkene, where the fixed bed reactor may include upflow, downflow, or other flow configurations. The fixed bed reactor may be operated liquid continuous, or may be operated at a boiling point of the reaction mixture, such as in a down flow boiling point reactor or a pulse flow reactor. In other embodiments, the fixed bed reactor may operate in the vapor phase. Operating conditions in the fixed bed reactor may be selected to achieve partial conversion of the alcohol, such as at least 25 weight percent of the alcohol, or at least 50 weight percent in other embodiments. In yet other embodiments, operating conditions in the fixed bed reactor may be selected to approach or achieve reaction equilibrium. The resulting mixture may then be fed to the distillation column reactor system for continued reaction and separation.

Due to the concurrent fractionation and separation of reactants and products, essentially complete conversion of the alcohol may be obtained in the distillation column reactor system. The success of the catalytic distillation approach lies in an understanding of the principles associated with distillation. Because the reaction is occurring concurrently with distillation, the desired reaction products, the dimers and the alkenes/isoalkenes, are removed from the reaction zone nearly as quickly as they are formed. This removal of the products minimizes the reverse reaction to form alcohols, which may be catalyzed by the same catalyst. Additionally, the reaction has an increased driving force because the reaction products have been removed and cannot contribute to the reverse reaction (Le Chatelier's Principle). Further, conditions in the distillation column reactor system may be maintained so as to essentially deadhead the alcohol within the column (i.e., maintaining overhead, bottoms, and reflux conditions to prevent recovery of the feed alcohol(s) in either the overheads and bottoms fractions). Substantially complete conversion, as used herein, refers to the conversion of at least 98 weight percent of the reactants (alcohols) to form products, including any byproducts. In other embodiments, at least 98.5 weight percent of the alcohol may be obtained; at least 99 weight percent in other embodiments; at least 99.5 weight percent in other embodiments; at least 99.8 weight percent in other embodiments; and at least 99.9 weight percent in yet other embodiments.

As mentioned above, the dimers, boiling at a temperature higher than water, may be recovered from the catalytic distillation reactor system as a bottoms fraction. Water and the alkenes or isoalkenes, and any unreacted alcohol, may be recovered as an overhead fraction.

The water and at least a portion of the hydrocarbons in the overheads fraction may be condensed in an overheads recovery system. The water and hydrocarbons may then be separated in a liquid/liquid separator. The liquid hydrocarbons recovered may be used as reflux for the column, may be recycled for further contact with the catalyst to produce additional dimers, and/or may be used for production of fuel range products as described below. The water may be withdrawn from the separator and treated for disposal or use in other processes as known in the art.

The dimers recovered from the catalytic distillation reactor system may be fed to a first reactor having one or more reaction zones containing an acid catalyst, which may be the same or different than the catalyst used in the pre-reactor or the catalytic distillation reactor system. The dimers may be contacted with the catalyst, where the dimers, or a portion thereof, may dissociate to form monomers (alkenes/isoalkenes) which may then react to form trimers. Oligomers (4+ units, as defined herein) may also be formed as a byproduct.

The effluent from the first reactor, including the trimers and any unreacted dimers, may then be fed along with hydrogen to a second reactor containing a hydrogenation catalyst. The olefinic dimers and trimers may then be contacted with the hydrogenation catalyst to hydrogenate the olefinic dimers and trimers to produce paraffins.

Acidic species may be present in the bottoms fraction recovered from the catalytic distillation reactor system and/or the effluent from the first (trimerization) reactor, due to acid throw from the catalysts, such as sulfur-containing acidic species. The acidic species may be removed from the effluent from the first reactor prior to feeding the effluent to the second reactor. Alternatively, the second reactor may contain a guard bed in front of the hydrogenation catalyst to limit the contact of acidic species with the hydrogenation catalyst. In other embodiments, the hydrogenation catalyst may be tolerant to the acidic species or may be used in a sufficient amount to negate the poisoning that may occur due to contact with the acidic species.

Following hydrogenation of the dimers and trimers, the effluent from the second reactor may be fed to a fractionator to separate the dimers from the trimers. The dimers may be recovered as an overheads fraction from the separator, and the trimers may be recovered as a bottoms fraction from the separator.

As described above, the desired trimer product may be produced directly from dimers in the first reactor, where the dimers may dissociate under reaction conditions to form the constituent isoalkenes, for example, which then react with themselves and/or the dimers to form the desired trimers. In other embodiments, it may be desired to produce trimers by reacting the dimers in the catalytic distillation reactor system bottoms fraction with alkenes recovered from the catalytic distillation reactor system as an overheads product. In such a case, at least a portion of the alkenes/isoalkenes recovered in the overheads fraction may be fed to the first reactor along with the dimers for contact with the acid catalyst.

In the first case, where the dimers dissociate, the dissociation of the dimers is an endothermic reaction, which may be used to control the temperature rise across the reaction zone. When the overheads and bottoms are both used to form the trimers, it may be desired to feed a diluent to the first reactor to control the temperature rise across the reaction zone. In some embodiments, a portion of the paraffinic hydrocarbons recovered as an overheads fraction from the separator following hydrogenation may be used as a diluent. In other embodiments, a portion of the paraffinic hydrocarbons recovered as a bottoms fraction from the separator following hydrogenation may be used as a diluent. In other embodiments, the paraffinic effluent from the hydrogenation reactor may be used as a diluent. It may also be desired to limit the temperature rise across the hydrogenation reaction zone, and hydrogenated dimer and/or trimer may also be recycled as a diluent for such purposes.

The portion of the paraffins not recycled to the trimerization reactor and/or the hydrogenation reactor may be recovered for use as a fuel, a fuel blend component, or for use in other processes as may be known to one skilled in the art. For example, when the alcohol is isobutanol, the alkene is isobutylene, the dimer is a C8, and the trimer is a C12, and the paraffins recovered from the fractionator following hydrogenation are C8 paraffins (in the overheads fraction) and C12 paraffins (in the bottoms fraction). The C8 paraffins may be used, for example, as a gasoline blending component. The C12 components may be used, for example, as a diesel, jet, kerosene range fuel blending component. The particular end use for the paraffinic dimers and trimers may depend upon the boiling point of the respective streams, or the boiling point range of the respective streams, such as where a mixture of starting alcohols are used and/or where the paraffinic trimer stream contains additional hydrogenated oligomers.

Catalysts useful in each of the pre-reactor, the catalytic distillation reactor system, and the trimerization reactor, as mentioned above, include various acidic catalysts. Isoolefin dimerization and trimerization, for example, is a catalytic reaction that may be performed using an acid resin catalyst. For example, oligomerization of isoolefins has been disclosed in U.S. Pat. Nos. 4,242,530, 4,375,576, 5,003,124, and 7,145,049, 6,335,473, 6,774,275, 6,858,770, 6,936,742, 6,995,296, 7,250,542, 7,288,693, 7,319,180, 6,689,927, 6,376,731, 5,877,372, 4,331,824, 4,100,220 and U.S. Patent Application Publication Nos. 20080064911, 20080045763, 20070161843, 20060030741, 20040210093, and 20040006252, among others. Processes for oligomerization of olefins over such resin catalysts require periodic shutdowns of the oligomerization unit to replace and/or regenerate the catalysts. Further, such solid-catalyzed processes may require additives ("selectivators") to promote the selectivity of the catalyst to the dimer, where the additives may result in unwanted acid throw, deactivating the catalyst, and may additionally require separation processes to remove the additive from the resulting product streams.

Catalysts useful in the pre-reactor, the catalytic distillation reactor system, and the trimerization reactor may include zeolites and metal substituted cationic resin catalysts, but other acidic or mildly acidic catalyst may also be used, including phosphoric acid treated clays. Naturally occurring zeolites have irregular pore size and are not generally considered as equivalent to synthetic zeolites. In some embodiments, however, naturally occurring zeolites are acceptable so long as they are substantially pure. The balance of the present discussion shall be directed to the synthetic zeolites with the understanding that natural zeolites are considered equivalent thereto as indicated above, i.e., in so far as the natural zeolites are the functional equivalents to the synthetic zeolites.

Synthetic zeolites may be prepared in the sodium form, that is, with a sodium cation in close proximity to each aluminum tetrahedron and balancing its charge. A number of principal types of molecular sieves have been reported, such as A, X, Y, L, erionite, omega, beta, and mordenite. The A-type molecular sieves have relatively small pore size. By the term pore size is meant the effective pore size (diameter) rather than the free pore size (diameter). X- and Y-type molecular sieves generally have a larger pore size (approximately 7.4 Angstroms) and differ as to the range of ratio of $SiO_2$ to $Al_2O_3$. Type L and other types listed have still higher ratios of $SiO_2$ to $Al_2O_3$, as known in the art.

Zeolite catalysts that may be used in embodiments disclosed herein are the acid form of the zeolite or at least exhibit acidic characteristics. The acid form is commercially available, but also may be prepared by treating the zeolites with acid to exchange Na for hydrogen. Another method to produce the acid form is to treat the zeolite with decomposable cations (generally ammonium ions) to replace Na with the decomposable ions and thereafter to heat the mole sieve to decompose the cation leaving the acid form. Generally the Na form is treated with ammonium hydroxide to remove the Na and thereafter the zeolite is heated to a temperature of about 350° C. to remove the ammonia. The removal of $Na^+$ ions with $NH_4^+$ is more easily carried out than with multivalent ions, as described below, and these catalysts are generally more active, but less stable to heat than the multivalent cation exchange forms. Zeolites, which have had their alkali metal reduced to low levels by partial treatment with $NH_4^+$ and partial multivalent metal cation exchange, may be expected to possess increased activity and increased stability.

Pore size within the crystal lattice may be significant in this reaction. According to one theory of molecular sieve catalytic activity, zeolite catalysis occurs primarily: inside the uniform crystal cavities; consequently, zeolitic catalyst activity depends on the number of aluminum atoms in the crystal and thus on the chemical composition of the crystal. Moreover, these catalytic sites are fixed within the rigid structure of the crystal, meaning that access to active sites can be altered by altering the structure of the crystal.

In some embodiments, resin catalysts may be used. For example, resin catalyst compositions such as sulfonic acid resins which have at least 50% of the sulfonic acid groups neutralized with one or more metal ions of Groups 4-12 of the Periodic Table, the rare earth metals, or mixtures thereof. The balance of the sulfonic acid groups may be neutralized with an alkali metal or alkaline earth metal, ammonium, or mixtures thereof. The sulfonic acid may be attached to any polymeric backbone. In some embodiments, the metal ions may include one or more of Ti, V, Cr, Mn, Fe, Co, Ni, Cu, Zn, Zr, Nb, Mo, Ru, Rh, Pd, Ag, Cd, Ta, W, Re, Pt, Ce, Nd, Sm, and Eu. The metal modified resin catalyst compositions are disclosed in U.S. Pat. Nos. 4,551,567 and 4,629,710, each of which is incorporated herein by reference.

The acid cation exchange resins are well known and have a wide variety of uses. The resins are cation exchangers that contain sulfonic acid groups which may be obtained by polymerization or copolymerization of aromatic vinyl compounds followed by sulfonation. Aromatic vinyl compounds suitable for preparing polymers or copolymers are: styrene, vinyl toluene, vinyl naphthalene, vinyl ethylbenzene, methyl styrene, vinyl chlorobenzene, and vinyl xylene. A large variety of methods may be used for preparing these polymers. For example, polymerization alone or in admixture with other monovinyl compounds, or by crosslinking with polyvinyl compounds, such as divinyl benzene, divinyl toluene, and divinylphenylether, among others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric and chlorosulfonic acid, or by copolymerizing aromatic compounds which contain sulfonic acid groups (see e.g., U.S. Pat. No. 2,366,007). Further sulfonic acid groups may be introduced into the polymers which already contain sulfonic acid groups; for example, by treatment with fuming sulfuric acid, i.e., sulfuric acid which contains sulfur trioxide. The treatment with fuming sulfuric acid is preferably carried out at 0 to 150.degree. C. and the sulfuric acid should contain sufficient sulfur trioxide so that it still contains 10 to 50% free sulfur trioxide after the reaction. The resulting products may contain an average of 1.3 to 1.8 sulfonic acid groups per aromatic nucleus. Particularly, suitable polymers containing sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, DE 908,247).

The ion exchange resin may have a granular size of about 0.25 to 1 mm, although particles from 0.15 mm up to about 2 mm may be used. The finer catalysts provide high surface area, but also result in high pressure drops through the reactor. The macroreticular form of these catalysts have a much larger surface area exposed and undergo limited swelling in a non-aqueous hydrocarbon medium compared to the gelular catalysts.

The metal modified catalyst may be prepared by contacting a macroporous matrix containing a sulfonic acid group with an aqueous solution of metal salts and solutions of alkali metal salts, alkaline earth metal salts, and/or ammonium salts to neutralize the acid groups. An alternative procedure for the preparation of the metal modified cation resin catalyst compositions comprises contacting a sulfonic acid cation exchange resin, e.g., a macroporous matrix of a polyvinyl aromatic compound crosslinked with a divinyl compound and having thereon from about 3 to 5 milliequivalents of sulfonic acid groups per gram of dry resin, (1) with an aqueous solution of a soluble metal salt as described above, such as Al, Fe, Zn, Cu, Ni, or mixtures thereof, to neutralize at least 50% to less than 100% of the available sulfonic acid groups with metal ions to produce a partially neutralized resin, and (2) thereafter contacting the partially neutralized resin with an aqueous solution containing a soluble compound of an alkali or alkaline earth metal of Groups 1 or 2, of the Periodic Table, or mixture thereof to neutralize the remaining sulfonic acid groups. In the final alkali neutralization step under the alternate procedure, care must be exercised to not contact the partially neutralized resin with a large excess of alkali or alkaline earth metal ions, (a slight excess, up to about 20%, beyond that required to neutralize the residual sulfonic acid groups may be used) since they appear to form double salts or possibly elute the metal ions, which may reduce the activity of the catalyst.

Resin catalyst composition useful herein may be characterized as a solid comprising a macroporous matrix of polyvinyl aromatic compound crosslinked with a divinyl compound and having thereon from about 3 to 5 milliequivalents of sulfonic acid groups per gram of dry resin, wherein at least 50 percent to less than 100 percent of said sulfonic acid groups are neutralized with a metal ion as described above; in other embodiments, at least 59 percent may be neutralized; and from about 70 percent to about 90 percent neutralized in yet other embodiments. Sulfonic acid groups not neutralized with the metal ion may be neutralized with alkali or alkaline earth metal ions of Group 1 or 2 of the Periodic Table, ammonium ions, or mixtures thereof.

The particulate catalyst may be employed by enclosing them in a porous container such as cloth, screen wire, or polymeric mesh. The material used to make the container may be inert to the reactants and conditions in the reaction system. Particles of about 0.1 5 mm size or pellets up to about ¼ inch diameter may be disposed in the containers.

The container used to hold the catalyst particles may have any configuration, such as the pockets disclosed in the commonly assigned patents noted above, or the container may be a single cylinder, sphere, doughnut, cube, tube, or the like. It is not essential that the spacing component entirely covers the catalyst component. It is only necessary that the spacing component intimately associated with the catalyst component act to space the various catalyst components away from one another as described above. Thus, the spacing component provides in effect a matrix of substantially open space in which the catalyst components are randomly but substantially evenly distributed. One such structure is that shown in U.S. Pat. No. 5,730,843, incorporated by reference herein. In addition, commonly assigned U.S. Pat. Nos. 4,443,559, 5,057,468, 5,262,012, 5,266,546, and 5,348,710 disclose a variety of catalyst structures for this use and are incorporated by reference herein.

U.S. Pat. No. 6,740,783, incorporated by reference herein, discloses other catalyst useful for the production of dialkyl ethers from alcohol, including crude alcohols containing some water. Disclosed are hydrophobic zeolites serving as a catalyst, such as USY, mordenite, ZSM-type, and Beta zeolites whose hydrogen cations are partially replaced with suitable metal ions, such as Group 1, 2, 11, or 12 metal ions, or ammonium ions. Other useful catalysts for the dehydration reaction are disclosed in U.S. Pat. No. 3,931,349.

Catalysts used in the fixed bed dehydration/dimerization reactor or trimerization reactors in various embodiments disclosed herein may include metal-treated zeolites, either acidic or basic, hydrofluoric acid-treated clays, and silica-alumina catalysts, such as a 20% silica-alumina, among the other catalysts described above. In some embodiments, hydrofluoric acid-treated clays may include those as disclosed in U.S. Patent Application Publication No. 2009-0178955A1, including the selectively poisoned hydrofluoric acid-treated clays disclosed therein, where the clays are selectively poisoned to control the acidity/activity thereof.

Catalysts used in the distillation column reaction zone in various embodiments disclosed herein may include metalized resins and silica-alumina catalysts, among the other catalysts described above. Metalized resin catalysts may include such catalysts as zinc-treated AMBERLYST 15 and copper-treated AMBERLYST 35, among others. AMBERLYST A70 may be used in other embodiments.

Operating conditions in the pre-reactor and the distillation column reactor may depend upon the purity of the alcohol feed, the particular alcohol(s) used, and the types of catalyst used in the pre-reactor (if present) and the distillation column reactor system, among other variables. Typical reaction zone operating conditions include temperatures ranging from 120° C. to 500° C. and pressures ranging from greater than 0 to 200 bar.

In some embodiments, pre-reactor temperatures may range from about 100° C. to about 300° C. (about 212 to about 572° F.). In other embodiments, pre-reactor temperatures may range from about 120° C. to about 260° C. (about 248 to about 500° F.); from about 150° C. to about 200° C. (about 302 to about 392° F.) in other embodiments; and from about 200° C. to about 240° C. (about 302 to about 464° F.), such as about 220° C. (about 428° F.), in yet other embodiments. In some embodiments, pre-reactor pressures may range from greater than 0 bar to about 200 bar (absolute). In other embodiments, pre-reactor pressures may range from about 1 bar to about 100 bar; from about 3 bar to about 50 bar in other embodiments; from about 5 bar to about 45 bar in other embodiments; and from about 20 to about 30 bar, such as about 25 bar, in yet other embodiments. The operating temperature and pressure selected may depend upon desired conversion and phase(s) of the reactants and products, among others.

The conditions used in the pre-reactor should be sufficient to dehydrate at least a portion of the alcohol. In other embodiments, more severe conditions may be used in the pre-reactor so as to dehydrate the alcohol and dimerize at least a portion of the resulting alkene.

The severity of operating conditions in the pre-reactor may also depend upon the amount of alcohol conversion required. The amount of alcohol conversion required may also affect the choice of catalyst used in the pre-reactor. For example, a desired pre-reactor conversion of 20 weight percent may require less severe operating conditions and/or a lower activity catalyst than for a pre-reactor conversion approaching equilibrium.

In some embodiments, the distillation column reactor system may include a reaction zone having temperatures in the range from about 50° C. to about 300° C. (about 122 to about 572° F.). In other embodiments, distillation column reactor system temperatures may be in the range from about 100° C. to about 260° C. (about 212 to about 500° F.); from about 150° C. to about 200° C. in other embodiments (about 302 to about 392° F.); and from about 170° C. to about 180° C. (about 338 to about 356° F.), such as about 170° C. (about 338° F.), in yet other embodiments. In some embodiments, the distillation column reactor system may include a reaction zone having a pressure in the range from about 1 bar to about 300 bar (absolute). In other embodiments, pressures in the reaction zone in the catalytic distillation reactor system may be in the range from about 2 bar to about 200 bar; from about 5 bar to about 100 bar in other embodiments; from about 10 bar to about 50 bar in yet other embodiments; and from about 10 bar to about 30 bar, such as about 20 bar, in yet other embodiments.

The temperature profile across the distillation column reaction zone should be sufficient to satisfy the kinetics of both the alcohol dehydration reaction and to dimerize at least a portion of the resulting olefin. The degree to which the olefin is dimerized may depend on the particular flow scheme selected. For example, where only dimer is used to produce trimers, it may be desired to maintain the operating conditions such that a significant amount of the alkene/isoalkene is dimerized. Where the dimer and olefin are used to produce trimers, the reaction conditions in the catalytic distillation reactor system may be maintained so as to produce a desired ratio of olefin to dimer, which may be greater than, equal to, or less than a stoichiometric ratio for the reaction of olefin plus dimer to form trimer. Where a greater than stoichiometric ratio is used, the excess olefins may also form dimers and/or trimers in the trimerization reaction zone, thus negating the need for additional downstream separation equipment (to recover olefin, dimer, and trimer separately).

The temperature profile in the catalytic distillation reactor system may also be sufficient to obtain substantially complete conversion of the alcohol. For example, for a catalyst having high activity, temperatures and pressures may be less severe than for a catalyst having a lower activity, where conditions for each may be selected to satisfy the kinetics of the dehydration reaction and to obtain substantially complete conversion of the alkyl alcohol.

The choice of catalyst and the severity of operating conditions in the distillation column reaction system may also be affected by the amount of alcohol conversion required. For example, the catalyst choice and conditions may be different for a pre-reactor conversion of about 20 weight percent as compared to a pre-reactor conversion approaching equilibrium.

Accordingly, the catalysts used in the distillation column reactor system may be the same or different than that used in the pre-reactor, when present. In some embodiments, it may be preferred to use a lower activity catalyst in the distillation column reactor system, thus allowing for extended catalyst life. The catalyst used in the pre-reactor may be of a higher activity, such as where pre-reactors are run in parallel, allowing for one to be repacked or regenerated while the other is operational.

Distillation column operating conditions may also depend upon the activity of the catalyst. For example, the amount of alcohol converted to olefin and the amount of olefin converted to dimer per distillation reaction stage may vary from 2 weight percent to 50 weight percent or more. Distillation column operating conditions, such as temperatures, pressures, and reflux ratios may also need to be adjusted to obtain substantially complete conversion of the alcohol. In some embodiments, reflux ratios may vary from about 0.1 or 0.5 to about 20; from about 0.5 to about 15 in other embodiments; from 0.6 to 10 in other embodiments; from 0.7 to 3 in other embodiments; and from 0.9 to 2.5 in yet other embodiments. In relation to alcohol and olefin conversion per distillation reaction stage, it has been found that higher reflux ratios are required at lower conversion per stage. For example, for an alcohol conversion per stage of approximately 20 weight percent, the reflux ratio may range from 2 to 3 to obtain complete conversion of the alcohol, such as a reflux ratio of about 2.4 in some embodiments. Comparatively, for an alcohol conversion per stage of approximately 40 weight percent, the reflux ratio may range from 0.5 to 2 to obtain complete conversion of the alcohol, such as a reflux ratio ranging from 1 to 1.6 in some embodiments.

Operating conditions in the trimerization reactor may depend upon the particular alcohol(s) used to produce the dimers and olefins, the particular flow scheme (trimer production with dimer alone or with olefin), the type(s) of catalyst used in the trimerization reactor, the desired conversion to trimer, and the tolerance in end products for oligomers, among other variables. Typical trimerization reaction zone operating conditions include temperatures in the range from 0° C. to 200° C. and pressures ranging from 1 to 50 bar.

In some embodiments, trimerization reactor temperatures may range from about 10° C. to about 120° C. (about 50 to about 248° F.). In some embodiments, trimerization reactor pressures may range from about 3 bar to about 200 bar (absolute). In other embodiments, trimerization reactor pressures may range from about 5 bar to about 100 bar; from about 10 bar to about 50 bar in other embodiments; from about 15 bar to about 45 bar in other embodiments; and from about 20 to about 30 bar, such as about 25 bar, in yet other embodiments.

In some embodiments, trimerization reactor inlet temperatures may range from about 35° C. to about 50° C. (about 95 to about 122° F.), where the temperature increases across the reaction zone due to the exothermic oligomerization reaction, and where the increase may be as little as 1 or 2° C. up to as much as 100° C. Regardless of the flow scheme used, it is desired to control the trimerization reaction such that a temperature rise across the reaction zone is less than about 50 or 60° C., for example. By limiting the temperature rise across the reactor, catalyst fouling may be reduced, providing for extended or reasonable catalysts cycle times. As mentioned above, a portion of the paraffinic end products may be used as a diluent to control the temperature rise. In some embodiments, a feed to diluent ratio may be in the range from about 0.1:1 to about 20:1; from about 1:1 to about 10:1 in other embodiments; and from about 1:1 to about 5:1 or 3:1 in yet other embodiments.

Catalysts useful in the hydrogenation reactor may include Group VIII metals, such as cobalt, nickel, palladium, or platinum, alone or in combination, and/or in combination with other metals, such as a Group V or Group VI metal, such as molybdenum or tungsten, on a suitable support, which may be alumina, silica, titania, silica-alumina, titania-alumina, titania-zirconia, or the like. Normally the catalytic metals are provided as the oxides of the metals supported on extrudates or spheres. Catalysts containing a Group VIB metal, such as molybdenum, and a Group VIII metal, such as cobalt or nickel, are preferred. Catalysts suitable for the hydrogenation reaction include cobalt-molybdenum, nickel-molybdenum and nickel-tungsten, among others. The metals may be reduced to the hydride form or other active states, if necessary, prior to use by exposure to hydrogen, for example.

The hydrogenation catalyst typically is in the form of extrudates having a diameter of ⅛, 1/16 or 1/32 inches and an L/D of 1.5 to 10. The catalyst also may be in the form of spheres having similar diameters. They may be directly loaded into standard single pass fixed bed reactors which include supports and reactant distribution structures.

The catalyst and operating conditions in the hydrotreatment/hydrogenation reactor may depend upon the particular alcohol(s) used to produce the dimers and trimers, the particular flow scheme (with or without guard beds to remove acid throw from the trimerization catalyst), the desired conversion to trimer and dimer to paraffins, and the tolerance in end products for any isomerization that may occur under hydrogenation conditions, among other variables. Typical hydrogenation reaction zone operating conditions include temperatures in the range from 100° C. to 500° C. and pressures ranging from 1 to 100 bar.

In some embodiments, hydrogenation reactor temperatures may range from about 100° C. to about 300° C. (about 212 to about 572° F.). In other embodiments, hydrogenation reactor temperatures may range from about 120° C. to about 260° C. (about 248 to about 500° F.); from about 130° C. to about 180° C. (about 266 to about 356° F.) in other embodiments; and from about 140° C. to about 170° C. (about 284 to about 338° F.) in yet other embodiments. In some embodiments, hydrogenation reactor pressures may range from about 3 bar to about 200 bar (absolute). In other embodiments, hydrogenation reactor pressures may range from about 5 bar to about 100 bar; from about 10 bar to about 50 bar in other embodiments; from about 15 bar to about 45 bar in other embodiments; and from about 20 to about 30 bar, such as about 25 bar, in yet other embodiments. If necessary to control temperature across the hydrogenation reactor, recycle of paraffinic products may be used as a diluent, where a ratio of diluent to feed may be in the range from about 0.1:1 to about 10:1; in other embodiments, the recycle to feed ratio may be in the range from about 1:1 to about 5:1; from about 1.5:1 to about 3.5:1 in yet other embodiments.

Referring now to FIG. 1, a simplified process flow diagram of a system for the production of jet or other heavy fuels from alcohols according to embodiments disclosed herein is illustrated. One skilled in the art would recognize that, although not depicted, pumps, valves, vessels, storage tanks, and other equipment commonly used for the processes described and illustrated herein are not shown so as to simplify the diagram. Additionally, while the following is described with respect to isobutanol as the alcohol feed, one skilled in the art would appreciate that other alcohols may also be used Isobutanol may be fed to a distillation column reactor system 10 via conduit 12. The feed location on distillation column reactor system 10 may be above, below, or intermediate a distillation reaction zone 14 containing a dehydration catalyst for converting at least a portion of the isobutanol to isobutylene and water and for dimerizing at least a portion of the isobutylene to form dimers of isobutylene. While the reaction is proceeding, the reaction products are concurrently fractionated, allowing isobutylene and water to be recovered as an overheads fraction 16 and isobutylene dimer to be recovered as a bottoms fraction 18.

Operating conditions, such as feed temperature, overheads temperature, bottoms temperature, the temperature profile of the column, feed rate, reflux ratio, and other operating variables may be selected to obtain substantially complete conversion of the isobutanol to isobutylene and water. In some embodiments, operating the distillation column reactor system may include maintaining a temperature profile across the distillation reaction zone to satisfy the kinetics of the dehydration reaction and partial dimerization of the isobutylene. In other embodiments, operating the distillation column reactor to obtain substantially complete conversion of the isobutanol may include maintaining a reflux rate above the reaction zone sufficient to separate the product isobutylene from the unreacted alcohol.

In yet other embodiments, the operating conditions may be selected such that the isobutanol is essentially dead-headed in the column. The temperature of the overhead fraction or upper column tray(s) may be sufficiently below the boiling point of the isobutanol, and the temperature of the bottom tray(s) may be sufficiently above the boiling point of the isobutanol such that the alcohol remains in the column until reacted.

The overheads fraction 16 may be partially condensed via indirect heat exchange in cooler 20, and the condensate may be collected in overhead drum 22. Water and isobutylene may form an azeotrope, and conditions in the overhead system should be maintained to condense essentially all of the water in the overheads fraction. The water and the condensed isobutylene may then be phase separated in overhead drum 22, where the isobutylene may be recycled to catalytic distillation reactor system 10 via flow line 24 and pump 26, and the water may be recovered via flow line 28. Non-condensed isobutylene may be recovered from overhead drum 22 and passed through chiller 30 to condense the isobutylene, recovered in drum 32. Lights and non-condensables may be recovered from drum 32 via flow line 34, and the isobutylene may be recovered from drum 32 via flow line 36.

The bottoms fraction 18, containing the dimers, may be fed to a fixed bed reactor 38 having a reaction zone 40 containing an acid catalyst for converting at least a portion of the isobutylene dimer to isobutylene trimer. If necessary, the dimer feed may be heated or cooled prior to contact with the catalyst via indirect heat exchange in heater 42.

After conversion of a portion of the dimer to trimer in reactor 38, the effluent from reactor 38 may be fed via flow line 44 to a fixed bed reactor 46 having a reaction zone 48 containing a hydrogenation catalyst for converting the olefinic dimers and trimers in the effluent to C8 and C12 paraffins. Hydrogen may be introduced via flow line 50 and fed along with the feed, as illustrated, or may be fed at multiple points along the length of reaction zone 48. If necessary, the dimer and trimer containing effluent from the trimerization reactor may be heated or cooled prior to contact with the hydrogenation catalyst via indirect heat exchange in heater 52.

The effluent from the hydrogenation reactor 46 may then be fed via flow line 54 to a fractionator 56 for separating the C8 paraffins from the C12 paraffins. The C8 paraffins may be collected as an overheads fraction via flow line 58 and the C12 paraffins may be collected via flow line 60. As noted above, the C8 and C12 paraffins may be used as fuels or fuel blendstocks appropriate for their boiling points.

Figure 2:
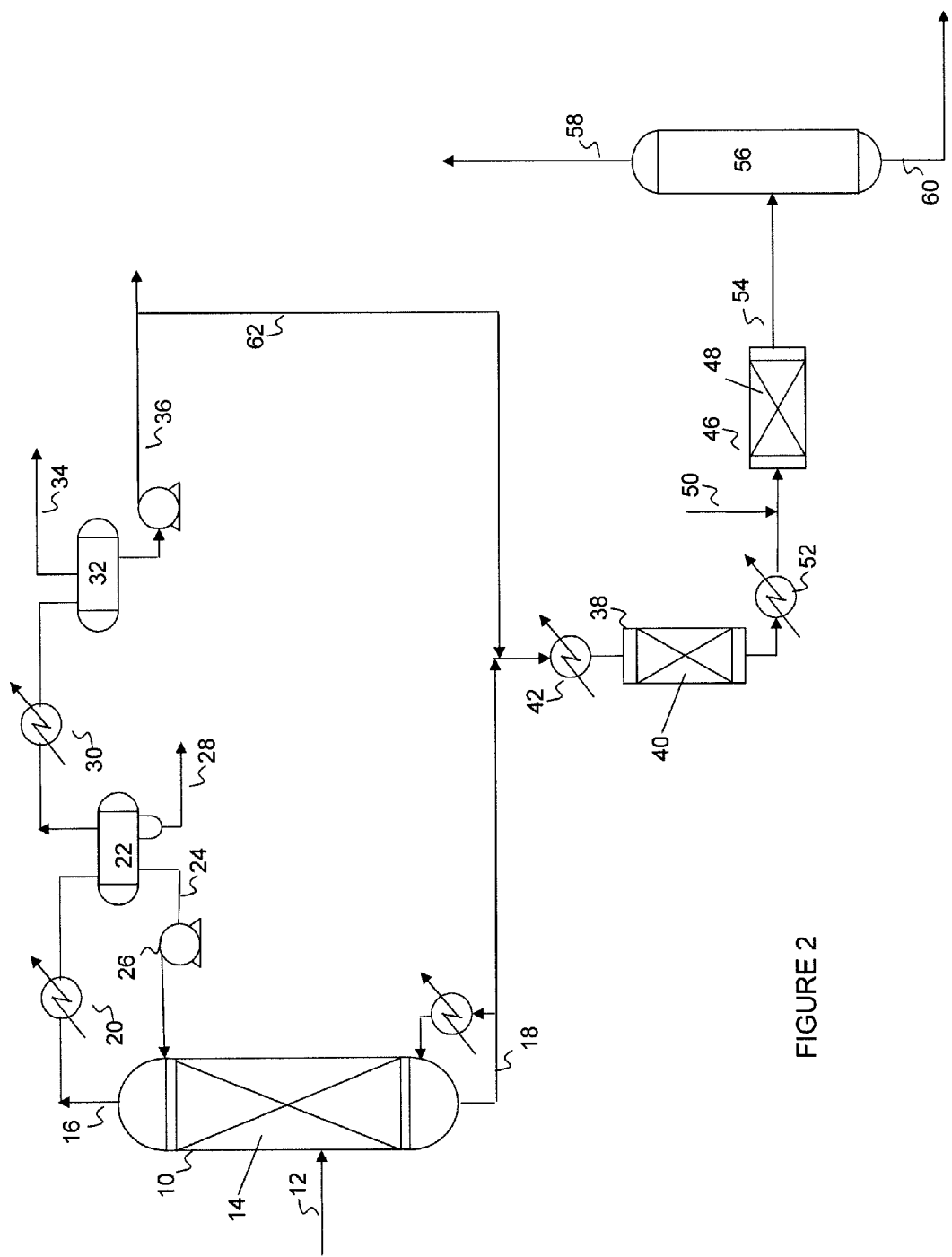
FIG. 2 is a simplified process flow diagram of a process for the production of jet and other heavy fuels according to embodiments disclosed herein.
Figure 3:
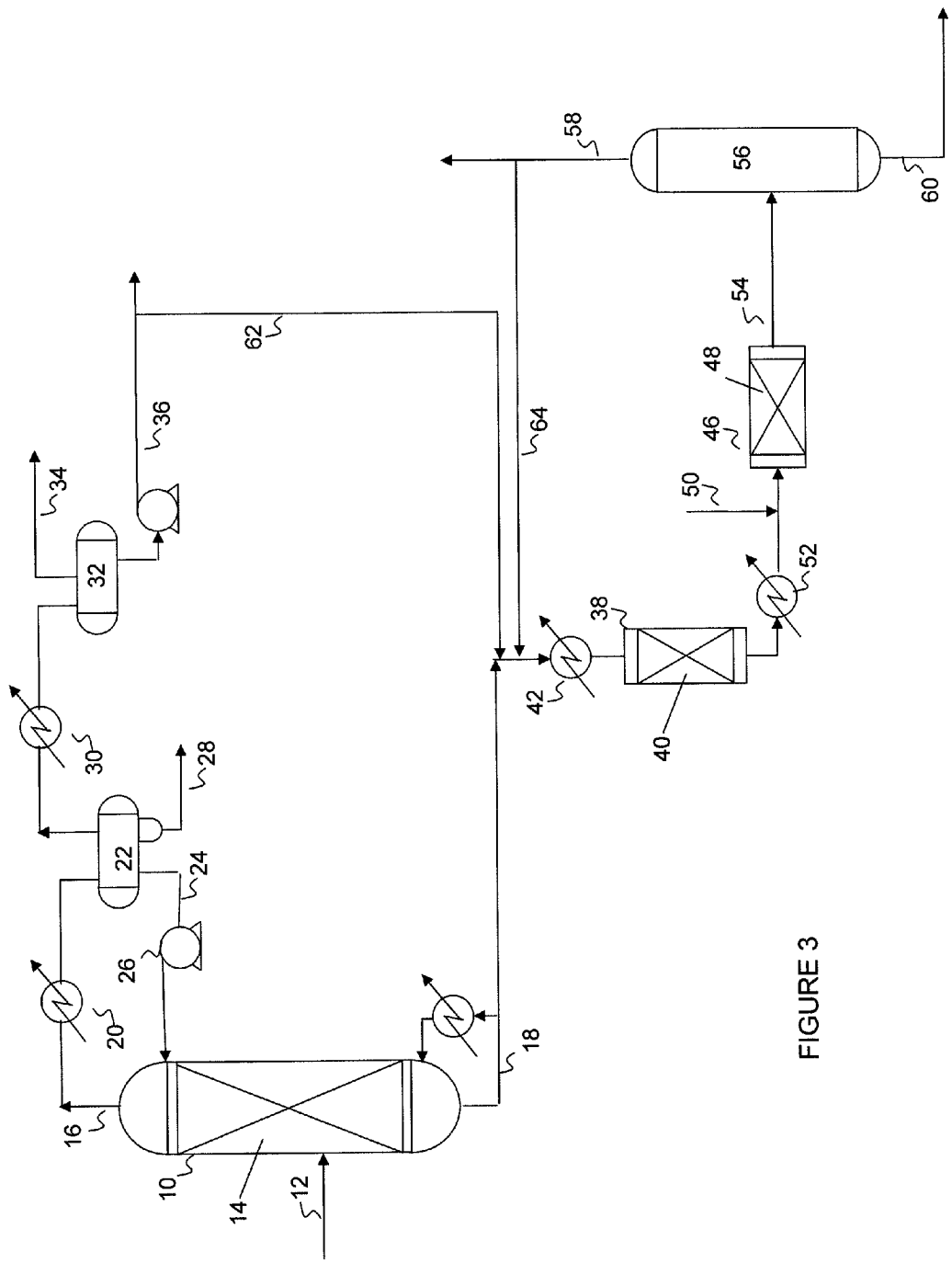
FIG. 3 is a simplified process flow diagram of a process for the production of jet and other heavy fuels according to embodiments disclosed herein.
Figure 4:
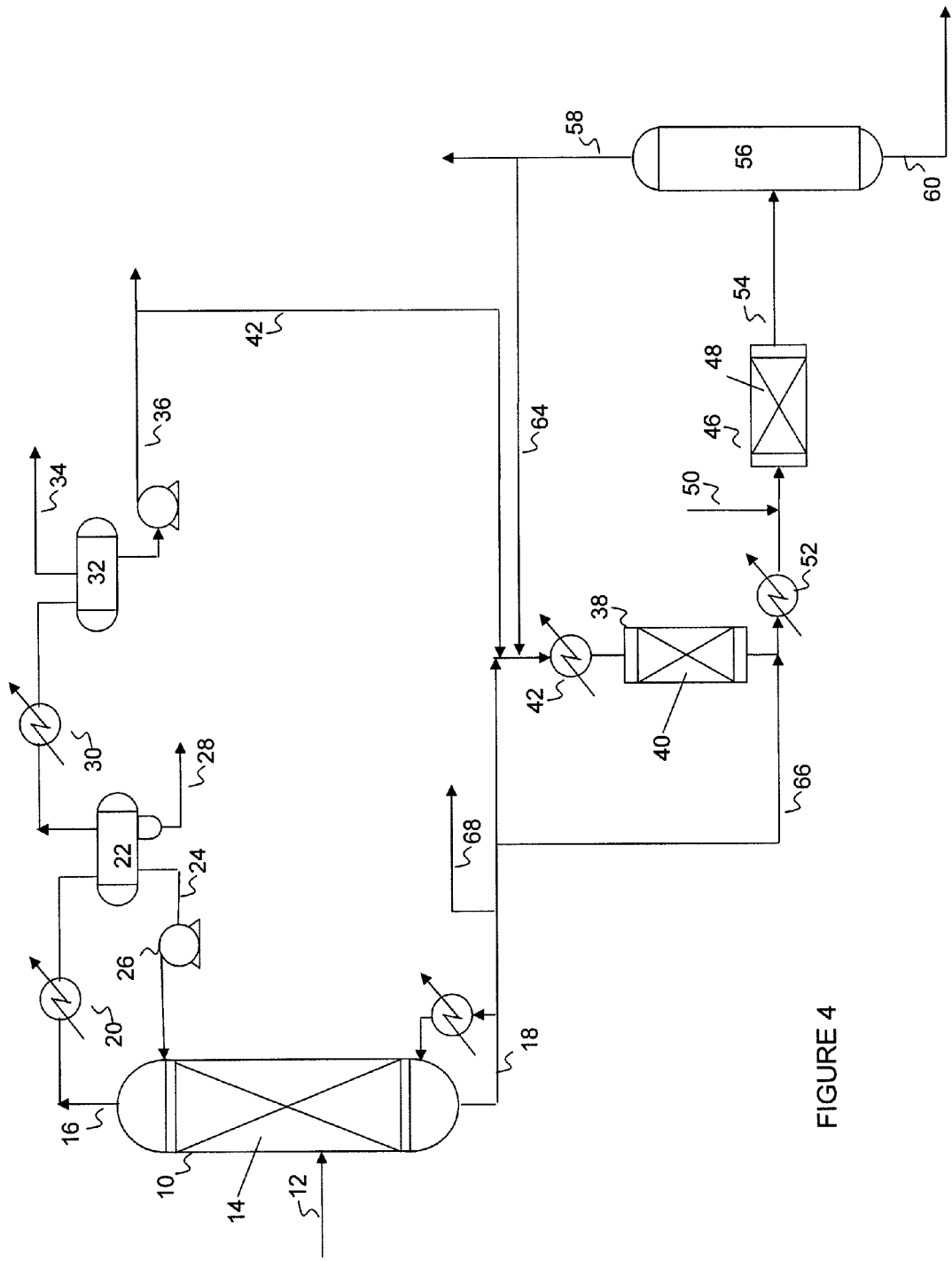
FIG. 4 is a simplified process flow diagram of a process for the production of jet and other heavy fuels according to embodiments disclosed herein.

FIGS. 2 through 4 introduce various features for the optional processing of the various streams produced during the process and for control of the temperature rise in the trimerization reactor.

Referring now to FIG. 2, a simplified process flow diagram of a system for the production of jet or other heavy fuels from alcohols according to embodiments disclosed herein is illustrated, where like numerals represent like parts. In this embodiment, a portion of the isobutylene recovered via flow line 36 is fed via flow line 62 to trimerization reactor 38 for reaction with itself and/or with the dimer fed via flow line 18.

Referring now to FIG. 3, a simplified process flow diagram of a system for the production of jet or other heavy fuels from alcohols according to embodiments disclosed herein is illustrated, where like numerals represent like parts. In this embodiment, as compared to FIG. 2, a portion of the C8 paraffins recovered via flow line 58 from fractionator 56 are recycled to the trimerization reactor 38 via flow line 64. The C8 paraffins recycled may act as a diluent in the trimerization reaction zone 40, limiting the temperature rise that may occur over the length of the reactor.

Referring now to FIG. 4, a simplified process flow diagram of a system for the production of jet or other heavy fuels from alcohols according to embodiments disclosed herein is illustrated, where like numerals represent like parts. In this embodiment, as compared to FIG. 3, two options for the dimer are shown. In the first, a portion of the dimer recovered via flow line 18 may bypass reactor 38 via flow line 66, proceeding directly to hydrogenation reactor 46. In this manner, the overall ratio of C8 to C12 products produced by the process may be controlled, such as to manage the product mixture to meet any fluctuations in demand that may occur over time. In the second, a portion of the dimer recovered via flow line 18 may be recovered via flow line 68 for use as a final product, such as a fuel or fuel blendstock, or as a reactant, such as to a downstream alkylation process, among others.

Referring again to FIG. 2, for example, the temperature, pressure, and activity and selectivity of the catalyst in reaction zone 14 of distillation column reactor system 10 may affect the mixture of products recovered in bottoms fraction 18. While dimers and/or trimers of butylenes are preferred, other products such as ethers may also be produced, such as via the reaction of isobutanol with isobutylene. The ethers formed may include, for example, diisobutyl ether, C12 ethers, and possibly others. The heavy oxygenated products recovered may then be included in the feed to oligomerization reactor 38 where they may add a mixture of tertiary butyl, isobutyl, and potentially higher alcohols to the products of reactor 38. These alcohols may be eliminated by using a catalytic distillation reactor like reactor 10 in place of the fixed bed reactor 38, or by fractionation of the product from reactor 38 and recycle to reactor 10. Any alcohols or ethers reaching hydrogenation reactor 46 may be converted to the corresponding constituent paraffins and water which may be separated from the dimers and trimers in column 56, and recovered in stream 58 which may then require additional fractionation before use as a liquid fuel. Thus, it is preferred to use a catalyst in reaction zone 14 that results in a minimal amount of heavy ethers.

In other embodiments, it may be desirable to produce a mixture of dimers and trimers of isobutylene with C8 and C12 ethers for use as a fuel, a fuel blendstock, or other downstream processing or products. In this scenario, catalytic distillation reactor system 10 may be used to produce such a blend, recovered as a separate product, and to concurrently produce and purify isobutylene for subsequent use in the production of olefin oligomers and paraffins useful as a jet fuel or other heavy fuels.

Figure 5:
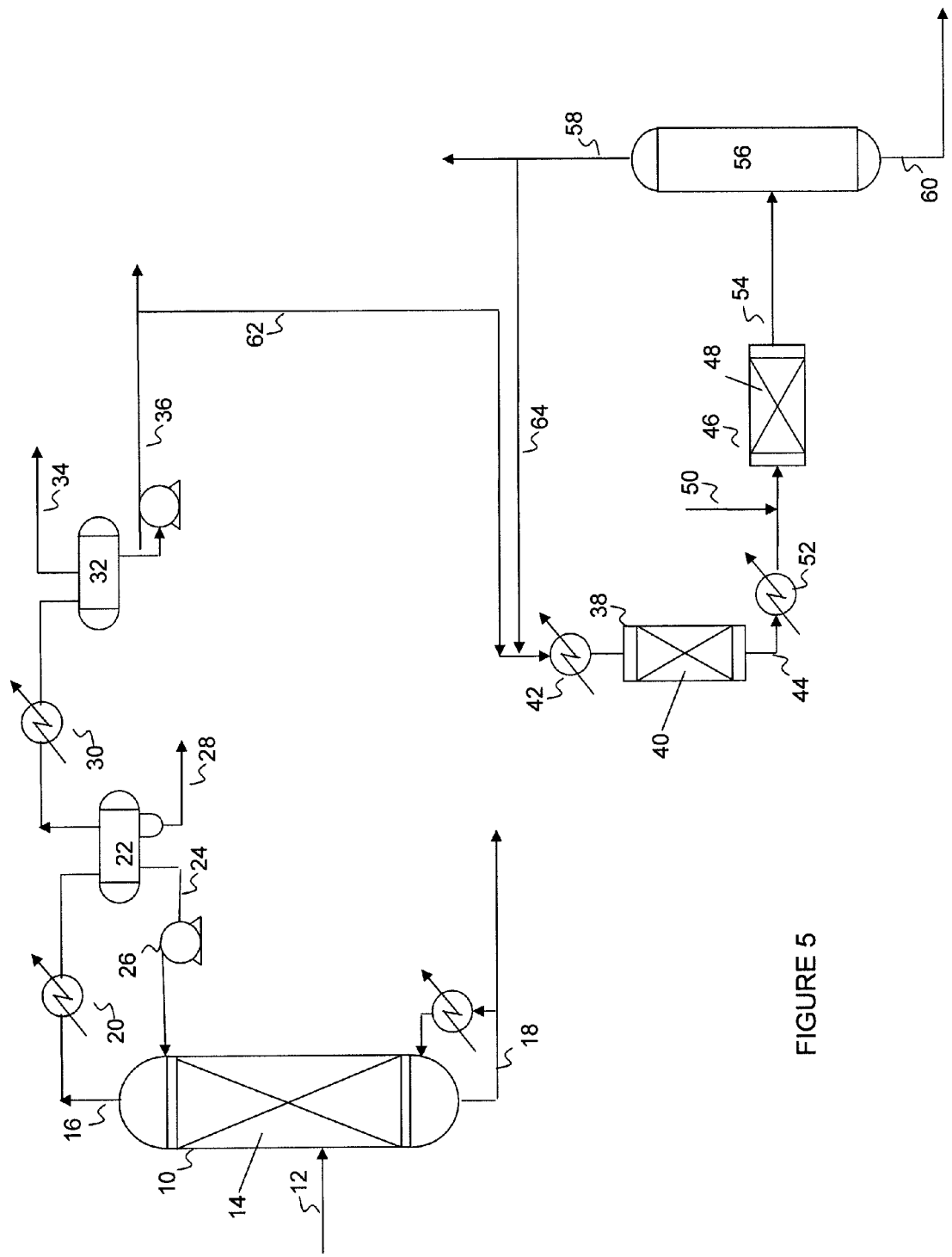
FIG. 5 is a simplified process flow diagram of a process for the production of jet and other heavy fuels according to embodiments disclosed herein.

Referring now to FIG. 5, a process for the production of jet or other heavy fuels is illustrated, where like numerals represent like parts. Similar to the process of FIG. 2, isobutanol may be fed to a distillation column reactor system 10 via conduit 12. The feed location on distillation column reactor system 10 may be above, below, or intermediate a distillation reaction zone 14 containing a dehydration catalyst for a) converting at least a portion of the isobutanol to isobutylene and water, b) dimerizing at least a portion of the isobutylene to form dimers of isobutylene, and c) reacting a portion of the isobutanol with product isobutylene or isobutylene oligomers to form C8+ ethers. While the reaction is proceeding, the reaction products are concurrently fractionated, allowing isobutylene and water to be recovered as an overheads fraction 16 and isobutylene dimer and the C8+ ethers to be recovered as a bottoms fraction 18. The bottoms fraction 18, containing the dimers and ethers may be recovered for use as a fuel, a fuel blendstock, or for other downstream processing.

The overheads fraction 16 may be partially condensed via indirect heat exchange in cooler 20, and the condensate may be collected in overhead drum 22. Water and isobutylene may form an azeotrope, and conditions in the overhead system should be maintained to condense essentially all of the water in the overheads fraction. The water and the condensed isobutylene may then be phase separated in overhead drum 22, where the isobutylene may be recycled to catalytic distillation reactor system 10 via flow line 24 and pump 26, and the water may be recovered via flow line 28.

Non-condensed isobutylene may be recovered from overhead drum 22 and passed through chiller 30 to condense the isobutylene, recovered in drum 32. Lights and non-condensables may be recovered from drum 32 via flow line 34, and the isobutylene may be recovered from drum 32 via flow line 36. In this manner, a high purity isobutylene product may be recovered for further processing. In some embodiments, the isobutylene fraction recovered via flow line 36 may contain greater than 90% isobutylene by weight; greater than 95% isobutylene by weight in other embodiments; greater than 98% isobutylene by weight in other embodiments; greater than 99% isobutylene by weight in other embodiments; and greater than 99.5% by weight isobutylene in yet other embodiments.

The high purity isobutylene feedstock recovered or a portion thereof may then be fed via flow line 62 to a fixed bed reactor 38 having a reaction zone 40 containing an acid catalyst for converting at least a portion of the isobutylene to isobutylene oligomers. If necessary, the isobutylene feed may be heated or cooled prior to contact with the catalyst via indirect heat exchange in heater 42. Also, if necessary, any water and/or alcohol remaining in the isobutylene fraction recovered may be separated prior to feeding of the isobutylene to the oligomerization reactor.

After conversion of a portion or all of the isobutylene in reactor 38, the effluent from reactor 38 may be fed via flow line 44 to a fixed bed reactor 46 having a reaction zone 48 containing a hydrogenation catalyst for converting the olefinic oligomers in the effluent to paraffins. Hydrogen may be introduced via flow line 50 and fed along with the feed, as illustrated, or may be fed at multiple points along the length of reaction zone 48. If necessary, the effluent from reactor 38 may be heated or cooled prior to contact with the hydrogenation catalyst via indirect heat exchange in heater 52.

The effluent from the hydrogenation reactor 46 may then be fed via flow line 54 to a fractionator 56 for separating C8 olefins and paraffins from the C12 paraffins. The C8 hydrocarbons may be collected as an overheads fraction via flow line 58 and the C12 paraffins may be collected via flow line 60. As noted above, the overhead and bottoms fractions recovered from column 56 may be used as fuels or fuel blendstocks appropriate for their boiling points.

Conversion of isobutanol to isobutane through the overall process illustrated by FIGS. 2-5 is undesired, as an outlet for the isobutane would be needed. As such, it is desired to convert as much of the isobutylene fed to reactor 38 to oligomers as possible. In some embodiments, conversion of isobutylene via oligomerization may be greater than 98% by weight; greater than 99% by weight in other embodiments; and greater than 99.5% by weight in other embodiments.

Similar recycle streams or process variations described above with respect to FIGS. 2-4 may also be used with the process as illustrated in FIG. 5. For example, a portion of overheads fraction 58 may be recycled via flow stream 64 to moderate the oligomerization reaction in reactor 38.

Other various embodiments as described above are not illustrated. However, one skilled in the art would readily be able to envision such flow schemes based upon the description and figures presented.

As described above, embodiments disclosed herein provide for the conversion of lower alcohols to form jet, diesel, and other heavier fuel-range products. While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the production of jet and other heavy fuels, the process comprising:
   contacting at least one C3 to C5 isoalkanol with a first catalyst to convert at least a portion of the isoalkanol to isoalkene, isoalkene dimers, and water;
   contacting at least a portion of the isoalkene dimers with a second catalyst, wherein the second catalyst comprises at least one of a metal modified resin catalyst, phosphoric acid treated clay, and HF treated clay, at a temperature in the range of 0° C. to 200° C. to convert at least a portion of the isoalkene dimers to isoalkene trimers via the reaction pathway: 3 dimer→2 trimers; and
   hydrotreating the isoalkene trimers to form isoalkanes useful as a jet fuel, kerosene, or other heavy fuels.

2. A process for the production of jet and other heavy fuels, the process comprising:
   feeding isobutanol to a catalytic distillation reactor system having at least one reaction zone containing a first catalyst;
   concurrently in the catalytic distillation reactor system:
   contacting the isobutanol with the first catalyst to convert at least a portion of the isobutanol to isobutylene, dimers of isobutylene, and water;
   fractionating the isobutylene and the water from the dimers of isobutylene;
   recovering the isobutylene and the water as an overheads fraction from the catalytic distillation reactor system;
   recovering the isobutylene dimers as a bottoms fraction from the catalytic distillation reactor system;
   feeding the bottoms fraction to a first reactor having at least one reaction zone containing a second catalyst, wherein the second catalyst comprises at least one of a metal modified resin catalyst, phosphoric acid treated clay, and HF treated clay;
   contacting the bottoms fraction with the second catalyst at a temperature in the range of 0° C. to 200° C. to convert at least a portion of the isobutylene dimers to trimers of isobutylene via the reaction pathway: 3 isobutylene dimer→2 isobutylene trimer;
   recovering an effluent from the reactor comprising the isobutylene trimers and any unreacted isobutylene dimers;
   feeding hydrogen and at least a portion of the effluent from the first reactor to a second reactor having at least one reaction zone containing a third catalyst;
   contacting the hydrogen and the effluent from the first reactor with the third catalyst to hydrogenate at least a portion of the isobutylene trimers to C12 paraffins and to hydrogenate at least a portion of any unreacted isobutylene dimers in the effluent to C8 paraffins;
   recovering an effluent from the second reactor comprising the C8 and C12 paraffins;
   separating the effluent from the second reactor in a fractionators;
   recovering the C8 paraffins as an overheads fraction from the fractionator; and
   recovering the C12 paraffins as a bottoms fraction from the fractionator.

3. The process of claim 2, wherein the first catalyst comprises at least one of a resin catalyst and a metal modified resin catalyst.

4. The process of claim 2, wherein the second catalyst comprises at least 50% of one or more sulfonic acid groups neutralized with one or more metal ions select from Groups 4-12 of the Periodic Table, the rare earth metals, or mixtures thereof.

5. The process of claim 2, wherein the third catalyst comprises at least one of a supported Ni/Mo catalyst, a supported Co/Mo catalyst, a supported Pd/Pt catalyst, and a supported Pt catalyst.

6. The process of claim 2, further comprising recycling at least a portion of the C8 paraffins, at least a portion of the C12 paraffins, or a combination thereof to the first reactor at a dimer to paraffin ratio in the range of 0.1:1 to 20:1.

7. The process of claim 2, further comprising separating the water from the isobutylene.

8. The process of claim 7, further comprising:
   feeding at least a portion of the isobutylene to the first reactor; and
   contacting the isobutylene and the isobutylene dimers with the second catalyst to react at least a portion of the isobutylene and isobutylene dimers to form isobutylene trimers.

9. The process of claim 2, further comprising recycling at least a portion of the isobutylene to the catalytic distillation reactor system as reflux.

10. The process of claim 2, further comprising at least one of recovering at least a portion of the isobutylene dimers, recovering at least a portion of the C8 paraffins, and recovering the isobutylene, and using the at least a portion of recovered isobutylene dimers, the portion of the C8 paraffins, or the isobutylene as a fuel, a fuel blendstock, or a reactant.

11. The process of claim 2, wherein the reaction zone in the catalytic distillation reactor system is at a pressure in the range of about 1 bar to about 300 bar and a temperature in the range of 50° C. to about 300° C.

12. The process of claim 2, wherein the reaction zone in the first reactor is at a pressure in the range of about 1 bar to about 50 bar and a temperature in the range of 10° C. to about 120° C.

13. The process of claim 2, wherein the reaction zone in the second reactor is at a pressure in the range of about 1 bar to about 100 bar and a temperature in the range of 100° C. to about 500° C.

14. The process of claim 2, further comprising maintaining conditions in the catalytic distillation reactor system to obtain substantially complete conversion of the isobutanol.

15. A process for the production of jet and other heavy fuels, the process comprising:
feeding isobutanol to a catalytic distillation reactor system having at least one reaction zone containing a first catalyst;
concurrently in the catalytic distillation reactor system:
contacting the isobutanol with the first catalyst to:
a) convert at least a portion of the isobutanol to isobutylene and water,
b) react the isobutylene produced to form dimers of isobutylene, and
c) reacting a portion of the isobutylene or dimers of isobutylene produced with isobutanol to form ethers;
fractionating the isobutylene and the water from the ethers and the dimers of isobutylene;
recovering the ethers and the isobutylene dimers as a bottoms fraction from the catalytic distillation reactor system;
recovering the isobutylene and the water as an overheads fraction from the catalytic distillation reactor system;
separating the overheads fraction to recover a water fraction and an isobutylene fraction;
feeding the isobutylene fraction to a first reactor having at least one reaction zone containing a second catalyst having activity for dissociation and alkylation, wherein the second catalyst comprises at least one of a metal modified resin catalyst, phosphoric acid treated clay, and HF treated clay;
contacting the isobutylene fraction with the second catalyst at a temperature in the range of 0° C. to 200° C. to convert at least a portion of the isobutylene to dimers of isobutylene, and to convert at least a portion of the dimers of isobutylene to trimers of isobutylene via the reaction pathway: 3 isobutylene dimer→2 isobutylene trimer;
recovering an effluent from the first reactor comprising the isobutylene dimers and trimers and any unreacted isobutylene;
feeding hydrogen and at least a portion of the effluent from the first reactor to a second reactor having at least one reaction zone containing a third catalyst;
contacting the hydrogen and the effluent from the first reactor with the third catalyst to hydrogenate at least a portion of the isobutylene dimers and trimers to paraffins;
recovering an effluent from the second reactor comprising C8 and C12 paraffins;
separating the effluent from the second reactor in a fractionator;
recovering the C8 paraffins as an overheads fraction from the fractionator, and
recovering the C12 paraffins as a bottoms fraction from the fractionator.

16. The process of claim 15, wherein the first catalyst comprises at least one of a resin catalyst and a metal modified resin catalyst.

17. The process of claim 15, wherein the third catalyst comprises at least one of a supported Ni/Mo catalyst, a supported Co/Mo catalyst, a supported Pd/Pt catalyst, and a supported Pt catalyst.

18. The process of claim 15, further comprising recycling at least a portion of the C8 paraffins, at least a portion of the C12 paraffins, or a combination thereof to the first reactor at a dimer to paraffin ratio in the range of 0.1:1 to 20:1.

19. The process of claim 15, further comprising recycling at least a portion of the overheads fraction to the catalytic distillation reactor system as reflux.

20. The process of claim 15, wherein the reaction zone in the catalytic distillation reactor system is at a pressure in the range of about 1 bar to about 300 bar and a temperature in the range of 50° C. to about 300° C.

21. The process of claim 15, wherein the reaction zone in the first reactor is at a pressure in the range of about 1 bar to about 50 bar and a temperature in the range of 10° C. to about 120° C.

22. The process of claim 15, wherein the reaction zone in the second reactor is at a pressure in the range of about 1 bar to about 100 bar and a temperature in the range of 100° C. to about 500° C.

23. The process of claim 15, further comprising maintaining conditions in the catalytic distillation reactor system to obtain substantially complete conversion of the isobutanol.

* * * * *